(12) United States Patent
Ramaiah

(10) Patent No.: US 9,457,064 B2
(45) Date of Patent: Oct. 4, 2016

(54) METHOD FOR TREATMENT OF VITILIGO

(76) Inventor: Abburi Ramaiah, New Delhi (IN)

( * ) Notice: Subject to any disclaimer, the term of this patent is extended or adjusted under 35 U.S.C. 154(b) by 948 days.

(21) Appl. No.: 11/193,165

(22) Filed: Jul. 29, 2005

(65) Prior Publication Data

US 2007/0027080 A1    Feb. 1, 2007

(51) Int. Cl.
| | |
|---|---|
| A61K 31/37 | (2006.01) |
| A61K 31/366 | (2006.01) |
| A61K 8/64 | (2006.01) |
| A61K 38/04 | (2006.01) |
| A61K 38/18 | (2006.01) |
| A61Q 19/02 | (2006.01) |
| C07K 14/50 | (2006.01) |

(52) U.S. Cl.
CPC ............. *A61K 38/1825* (2013.01); *A61K 8/64* (2013.01); *A61K 31/366* (2013.01); *A61K 31/37* (2013.01); *A61K 38/04* (2013.01); *A61Q 19/02* (2013.01); *C07K 14/503* (2013.01)

(58) Field of Classification Search
CPC ...... A61K 31/37; A61K 31/366; A61K 8/64; A61K 38/04; A61K 38/1825; A61Q 19/02; C07K 14/503
See application file for complete search history.

(56) References Cited

U.S. PATENT DOCUMENTS 6,143,723 A    11/2000  Ramaiah

FOREIGN PATENT DOCUMENTS

| AU | 722626 | 8/2000 |
|---|---|---|
| IN | 185613 | 3/2001 |
| IN | 185703 | 4/2001 |
| IN | 186437 | 9/2001 |

OTHER PUBLICATIONS

Grimes, P.E. Psoralen photochemotherapy for vitiligo. Clinics in Dermatology. 1997. vol. 15, pp. 921-926.*
Valkova S, et al. Treatment of vitiligo with local khellin and UVA: comparison with systemic PUVA. Clinical and Experimental Dermatology. 2004. vol. 29, p. 180-184.*
Kim, S. M. et al. The efficacy of low-dose oral corticosteroids in the treatment of vitiligo patients. International Journal of Dermatology, 1999, vol. 38, p. 546-550.*
Malakar, S. et al. Treatment of stable and recalcitrant vitiligo by autologous miniature punch grafting: a prospective study of 1,000 patients. Dermatology, 1999, vol. 198, p. 133-139.*
Leeuw et al., "A case study to evaluate the treatment of vitiligo with khellin encapsulated in L phenylalanin stabilized phosphatidylcholine liposomes in combination with ultraviolet light therapy", European Journal of Dermatology, vol. 13, No. 5, (Sep. 2003), pp. 474-477.
Carlie et al., "KUVA (khellin plus ultraviolet A) stimulates proliferation and melanogenesis in normal human melanocytes and melanoma cells in vitro", British Journal of Dermatology, vol. 149, (2003), pp. 707-717.

* cited by examiner

*Primary Examiner* — Robert Landsman
*Assistant Examiner* — Bruce D Hissong
(74) *Attorney, Agent, or Firm* — The Webb Law Firm

(57) ABSTRACT

Synergistic therapies for the treatment of vitiligo are provided, in which basic fibroblast growth factor peptide(s) lotion was developed as a new mode of therapy for the treatment of vitiligo. It went through various phases of successful clinical trials in India and is marketed by the drug controller general (India). It is effective in 80% of stable and segmental vitiligo. Data are provided which demonstrate that combinatorial treatment of vitiligo by local application of bFGF peptide(s) lotions in association with psoralens and UV-A, or steroids or surgical procedures, produce a synergistic response in which the rate of repigmentation increases synergistically and more efficacious results are obtained than with any one of them alone. Any combinatorial therapy comprising the local application of bFGF peptide(s) lotion on the vitiligo patch in combination with any other therapies for the treatment of vitiligo also may act synergistically.

5 Claims, 8 Drawing Sheets

SEQUENCE LISTING

<160> NUMBER OF SEQ ID NOS: 8

<210> SEQ ID NO 1
<211> LENGTH: 10
<212> TYPE: PRT
<213> ORGANISM: Artificial Sequence
<220> FEATURE:
<221> NAME/KEY:
<223> OTHER INFORMATION: Synthetic nonbacterial source

<400> SEQUENCE: 1

Tyr Arg Ser Arg Lys Tyr Ser Ser Trp Tyr
1               5                   10

<210> SEQ ID NO 2
<211> LENGTH: 10
<212> TYPE: PRT
<213> ORGANISM: Artificial Sequence
<220> FEATURE:

```
<221> NAME/KEY:
<223> OTHER INFORMATION: Synthetic nonbacterial source

<400> SEQUENCE: 2

Tyr Arg Ser Arg Lys Tyr Glu Ser Trp Tyr
1               5                   10

<210> SEQ ID NO 3
<211> LENGTH: 10
<212> TYPE: PRT
<213> ORGANISM: Artificial Sequence
<220> FEATURE:
<221> NAME/KEY:
<223> OTHER INFORMATION: Synthetic nonbacterial source

<400> SEQUENCE: 3

Tyr Arg Ser Arg Lys Tyr Glu Ser Trp Tyr
1               5                   10

<210> SEQ ID NO 4
<211> LENGTH: 11
<212> TYPE: PRT
<213> ORGANISM: Artificial Sequence
<220> FEATURE:
<221> NAME/KEY:
<223> OTHER INFORMATION: Synthetic nonbacterial source

<400> SEQUENCE: 4

Gly Tyr Arg Ser Arg Lys Tyr Ser Ser Arg Tyr
1               5                   10

<210> SEQ ID NO 5
<211> LENGTH: 15
<212> TYPE: PRT
<213> ORGANISM: Artificial Sequence
<220> FEATURE:
<221> NAME/KEY:
<223> OTHER INFORMATION: Synthetic nonbacterial source

<400> SEQUENCE: 5

Tyr Arg Ser Arg Lys Tyr Ser Ser Trp Tyr Val Ala Leu Lys Arg
1               5                   10                  15

<210> SEQ ID NO 6
<211> LENGTH: 24
<212> TYPE: PRT
<213> ORGANISM: Artificial Sequence
<220> FEATURE:
<221> NAME/KEY:
<223> OTHER INFORMATION: Synthetic nonbacterial source

<400> SEQUENCE: 6

Pro Ala Leu Pro Glu Asp Gly Gly Ser Gly Ala Phe Pro Pro Gly His
1               5                   10                  15

Phe Lys Asp Pro Lys Arg Leu Tyr
            20

<210> SEQ ID NO 7
<211> LENGTH: 10
<212> TYPE: PRT
<213> ORGANISM: Artificial Sequence
<220> FEATURE:
<221> NAME/KEY:
<223> OTHER INFORMATION: Synthetic nonbacterial source

<400> SEQUENCE: 7

Tyr Arg Ser Arg Lys Tyr Ser Ser Trp Tyr
```

```
<210> SEQ ID NO 8
<211> LENGTH: 10
<212> TYPE: PRT
<213> ORGANISM: Artificial Sequence
<220> FEATURE:
<221> NAME/KEY:
<223> OTHER INFORMATION: Synthetic nonbacterial source

<400> SEQUENCE: 8

Tyr Arg Ser Arg Lys Tyr Ser Ser Trp Tyr
1               5                   10
```

METHOD FOR TREATMENT OF VITILIGO

FIELD OF THE INVENTION

This invention relates to a method of treating vitiligo using synergistic Formulations.

BACKGROUND OF THE INVENTION

Vitiligo/leucoderma is an acquired depigmentation of skin characterized by patchy loss of pigment that becomes progressive with time. This disorder affects about 1% of the world population. Traditional therapies for vitiligo mainly include photo chemotherapy with topical/oral psoralens followed by exposure to ultra violet A radiation (PUV-A) or topical/oral steroids. PUV-A therapy is perhaps the main stay in the treatment of vitiligo. However only about 50% of cases get repigmentation. More over in a patient in response to PUV-A, many vitiligo patches may repigment partially only and the rest of the patches may remain unresponsive to PUV-A therapy even after long duration of treatment. The repigmentation in the above therapies is a result of multiplication of melanocytes, the cells, which produce the pigment melanin in the skin. The multiplication of melanocytes in response to the above therapies occur from the margins of the vitiligo patch or at the pigmented hair follicles and their migration/spread to the vitiligo patch.

Basic fibroblast growth factor (bFGF) also known as FGF2 so named because it contains a high number of basic amino acid residues (Lysine, Arginine and Histidine) is a potent mitogen for a variety of cell types including melanocytes. Both human and bovine bFGF were isolated and the gene expressing this product were sequenced and cloned. In addition bFGF was found to be expressed in a wide variety of tissue types including placenta, keratinocytes and fibroblasts. The bFGF or its agonist peptides were tested on human volunteers in the various phases of clinical trials in India and found to be successful in repigmenting about 80% of volunteers with stable generalised vitiligo and segmental vitiligo. Patents of interest describing bFGF or agonist peptides and the formulation for their penetration through intact skin include U.S. Pat. No. 6,143,723, Australian patent 722626, Indian patents 185613, 186437 and 185703.

Vitiligo is a pigmentary disorder with patchy loss of skin pigment melanin, (Ramaiah. A, Puri. N, Mojamdar M, A new hypothesis for the etiology of vitiligo, Acta Derm, Venerol (Stockholm), 1989, 69, 323-327) postulated that deprivation of a mitogen(s) like basic fibroblast growth factor (bFGF) for melanocytes or its decreased level in the skin of vitiligo patients for as at unknown reason could result in the loss of melanin producing cells melanocytes in skin resulting in vitiligo. Basic fibroblast growth factor (bFGF) also known as FGF2 is a potent mitogen for variety of cell types including melanocytes. Both human and bovine bFGF have been isolated and the gene expressing this product have been sequenced and cloned. In addition bFGF has been found to be expressed in a wide variety of tissue types including pituitary, brain and adrenal gland corpusluteum, retina, kidney, placenta and keratinocytes, fibroblasts. The above hypothesis that a mitogen like bFGF may be reduced in its levels in vitiligo patch resulting in loss of melanocytes and the pigment melanin in vitiligo skin was supported recently from studies by others (Moretti S et al. Insight in to the pathogenesis of vitiligo, Imbalance of epidermal cytokines at sites of lesions, Pig. Cell. Res 2002, 15.

SUMMARY OF THE INVENTION

According to this invention there is provided a method for combinatorial synergistic therapy for treatment of generalized vitiligo and segmental vitiligo comprises local application of an effective amount of a composition comprising 0.02 to 5% w/w of at least one peptide selected from a group consisting of bFGF amino acids 106-115 (Seq ID NO 1), bFGF amino acids 106-120 (Seq ID NO 5), bFGF amino acids 1-24 (Seq ID NO 6), Seq ID NO: 2, 3, 4, 7, and 8 as described in U.S. Pat. No. 6,143,723 in the formulation as described in the U.S. Pat. No. 6,143,723 along with psoralens and UV-A (PUV-A therapy)/PUV-ASOL.

The method of combinatorial synergistic therapy for treatment of vitiligo patches not responding to PUV-A therapy comprises local application of an effective amount of a composition comprising 0.02-5% w/w of at least one peptide selected from a group consisting of bFGF amino acids 106-115 (Seq ID NO 1), bFGF amino acids 106-130 (Seq ID NO 5), bFGF amino acids 1-24 (Seq ID NO 6), Seq ID NO: 2, 3, 4, 7 and 8 as described in U.S. Pat. No. 6,143,723 in the formulation as described in U.S. Pat. No. 6,143,723 along with continuing the oral intake of psoralens and exposure to UV-A.

The method of combinatorial synergistic therapy for treatment of fast spreading vitiligo comprises local application of an effective amount of a composition comprising 0.02-5% w/w of at least one peptide selected from a group consisting of bFGF amino acids 106-115 (Seq ID NO 1), bFGF amino acids 106-120 (Seq ID NO 5), bFGF amino acids 1-24 (Seq ID NO 6), Seq ID NOs: 2, 3, 4, 7 and 8 as described in the U.S. Pat. No. 6,143,723 in the formulation as described in the U.S. Pat. No. 6,143,723 along with steroid therapy.

The method for combinatorial synergistic therapy for treatment of vitiligo comprises local application of an effective amount of composition comprising 0.02% to 5% w/w of at least one peptide selected from a group consisting of bFGF aminoacids 106-115 (SEQ ID NO 1), bFGF amino acids 106-120 (SEQ ID NO 5), bFGF aminoacids 1-24 (SEQ ID NO 6), SEQ ID: 2, 3, 4, 7 and 8 as described in the U.S. Pat. No. 6,143,723 in the formulation as described in the U.S. Pat. No. 6,143,723 along with surgical procedures. The method for combinatorial synergistic therapy for treatment of vitiligo comprises local application of the composition further comprises 10-50% w/w of solvent, 10-40% w/w of glycols, and 10-40% w/w of at least one penetration enhancing agent.

The local application of the bFGF peptide(s) in the formulation described in the U.S. Pat. No. 6,143,723 is effective in more than 80% of cases of stable generalised vitiligo or segmental vitiligo. It is felt that the speed of repigmentation and even better out come than 80% success rate may be accomplished if it is combined with the traditional therapies like PUV-A therapy for vitiligo. In addition bFGF peptide lotion therapy is not effective to prevent the fast spread of vitiligo and perhaps a synergistic combinatorial therapy may emerge if bFGF peptide lotion therapy is used in combination with the steroid therapy traditionally used in the case of fast spreading vitiligo. Similarly the local application the bFGF peptide(s) lotion therapy may be advantageously used with any other therapy including the surgical or other therapies involving immuno modulators. Synergistic Combinatorial Therapy for Treatment of Fast Spreading Vitiligo Cases Comprising the Peptide(s) in the Formulation Described in the U.S. Pat. No. 6,143,723 and Steroid Therapy.

The bFGF peptide(s) lotion therapy is effective for stable vitiligo or segmental vitiligo but not for fast spreading vitiligo.

Steroid therapy is the only therapy available in the presently known methods of treatment to Treat fast spreading vitiligo (Kendel E, Vitiligo response to 02% betamethasone 17-valerate In flexible collodin. Dermetologica, 1970, 141, 277-281). However prolonged therapy with steroid produce many side effects (Geraldiz C B, Gutierrez G T, A clinical trail of clobetasol Propionate in Filipino vitiligo patients. Clinical Therapy, 1987, 9, 474-482, Ortonne J, Clinical Dermatol 1989, 7, 120-135). In addition after stoppage of treatment, the disease reoccurs. The Mode of action of steroids in stopping the fast spread of vitiligo and repigmentation was Thought to be brought about by its inhibitory effect on production of auto anti bodies to Melanocytes which were shown to be responsible for the fast spread of vitiligo macules (Han K, Chen D, Bystryn J C, Systemic steroids suppress antimelonocyte antibodies in vitilligo, J. Cutan. Med. Surg. 1997, 1, 193-195). It was thought therefore possible that the combinatorial therapy for treatment of vitiligo with local application of bFGF peptide(s) lotion along with oral steroids may accomplish dual goals, that is 1. Arrest of past spread of vitiligo
2. Faster repigmentation of vitiligo macules.

BRIEF DESCRIPTION OF THE DRAWINGS

FIG. 1 (*b*) is the representation of vitilligo after treatment with topical bFGF peptide lotion.

FIG. 2 (*b*) is the representation of fast spreading vitilligo after treatment with combination of steroid and topical bFGF peptide lotion.

FIG. 3 (*b*) is the representation of vitilligo after the treatment with combination of topical bFGF peptide lotion and PUVASOL.

FIG. 4 (*b*) is the representation of vitilligo after the treatment with topical bFGF peptide lotion and PUVASOL.

FIG. 5 (*b*) is the representation of vitilligo resistant for more than a year for PUV-A after the treatment with topical peptide bFGF lotion and PUV-A.

FIG. 8 (*b*) L is the representation of vitilligo after punch grafting and after the treatment with bFGF peptide lotion for 2 months. R is the control.

DETAILED DESCRIPTION OF THE INVENTION

Example: 1

Figures 1A, 1B:
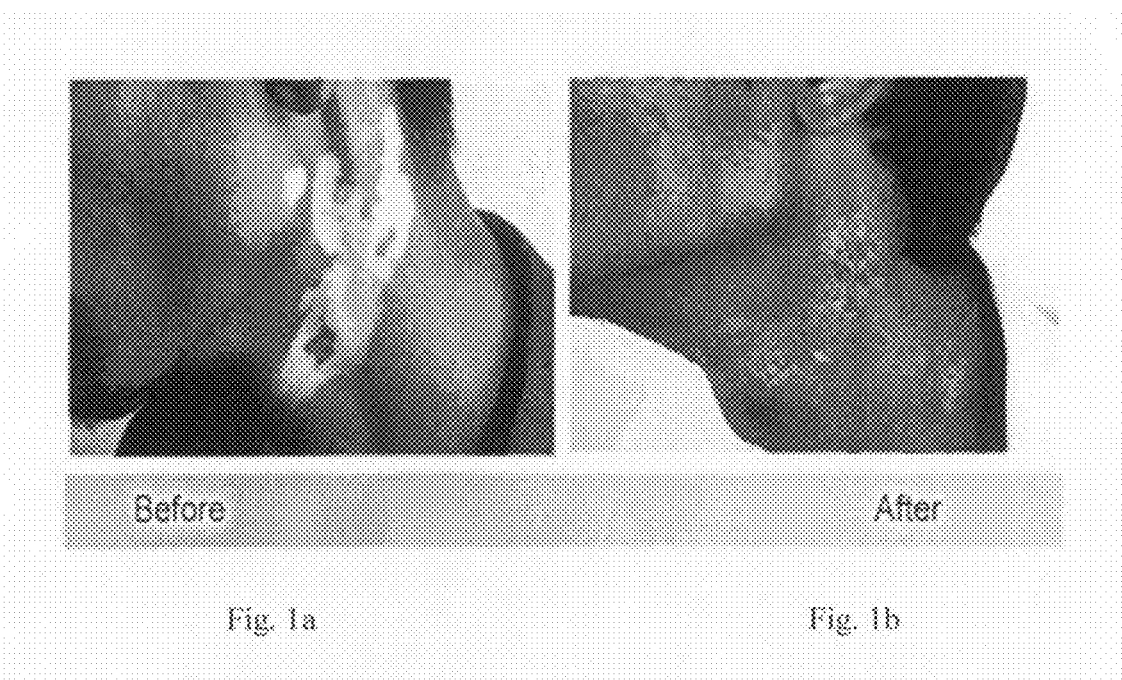
FIG. 1 (*a*) is the representation of vitiligo before treatment with topical bFGF peptide lotion.

As a typical illustration of efficacy of bFGF peptide(s) in repigmentation of vitiligo patch of human volunteers (FIG. 1*a*, 1*b*) were depicted. FIG. 1*a* was the size of the vitiligo patch before start of treatment with bFGF peptide lotion and 1*b* was of the same patch after local application of the bFGF peptide(s) lotion for a period of 6 months. However the above treatment was effective in 80% of stable vitiligo and in segmented vitiligo cases (See Table—1, 2 for more details).

Patents of interest describing bFGF or agonist peptides derived from it for use as pigmentary agents include U.S. Pat. No. 6,143,723, Australian Patent NO: 722626, Indian Patents 185613, 186437 186703.

The local application of bFGF peptide(s) in the formulation described in the U.S. Pat. No. 6,143,723 is effective in more than 80% of cases of stable generalised vitiligo or segmental vitiligo. It is felt that the speed of repigmentation and even better out come than 80% success rate may be accomplished if it is combined with the traditional therapies like PUV-A therapy for vitiligo. In addition bFGF peptide(s) lotion therapy is not effective to prevent the fast spreading of vitiligo and perhaps a synergistic combinatorial therapy may emerge if bFGF peptide lotion therapy is used in combination with the steroid therapy traditionally used in the case of fast spreading vitiligo. Similarly the local application bFGF peptide(s) lotion therapy may be advantageously used with any other therapy including the surgical therapies.

Example: 2

The mode of action of steroids in stopping the fast spread of vitiligo and repigmentation was thought to be brought about by its inhibitory effect on production of auto anti bodies to melanocytes which were shown to be responsible for the fast spread of vitiligo macules (Han K, Chen D, Bystryn J C, Systemic steroids suppress antimelonocyte antibodies in vitilligo, J. Cutan. Med. Surg. 1997, 1, 193-195). It was thought therefore possible that the combinatorial therapy for treatment of vitiligo with local application of bFGF peptide(s) lotion along with oral steroids may accomplish dual goals, that is 3. Arrest of past spread of vitiligo
4. Faster repigmentation of vitiligo macules.

Figures 2A, 2B:
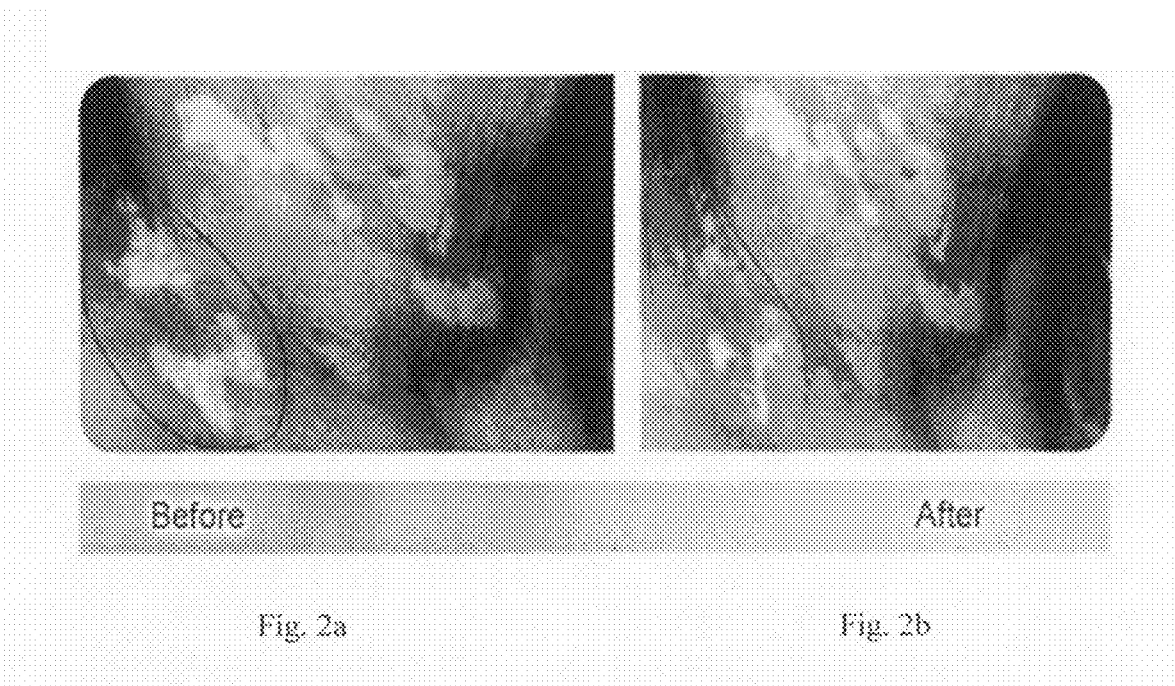
FIG. 2 (*a*) is the representation of fast spreading vitiligo before treatment with combination of steroid and topical bFGF peptide lotion.
Figures 3A, 3B:
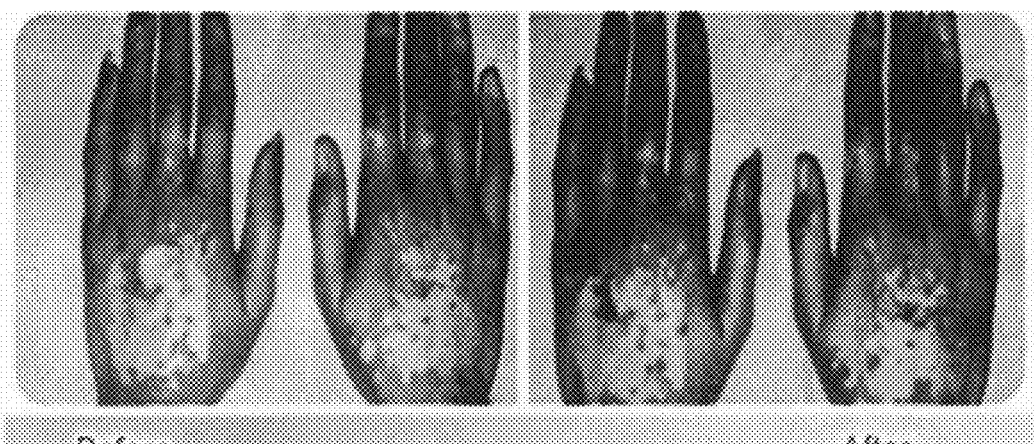
FIG. 3 (*a*) is the representation of vitiligo before the treatment with combination of topical bFGF peptide lotion and PUVASOL.
Figures 4A, 4B:
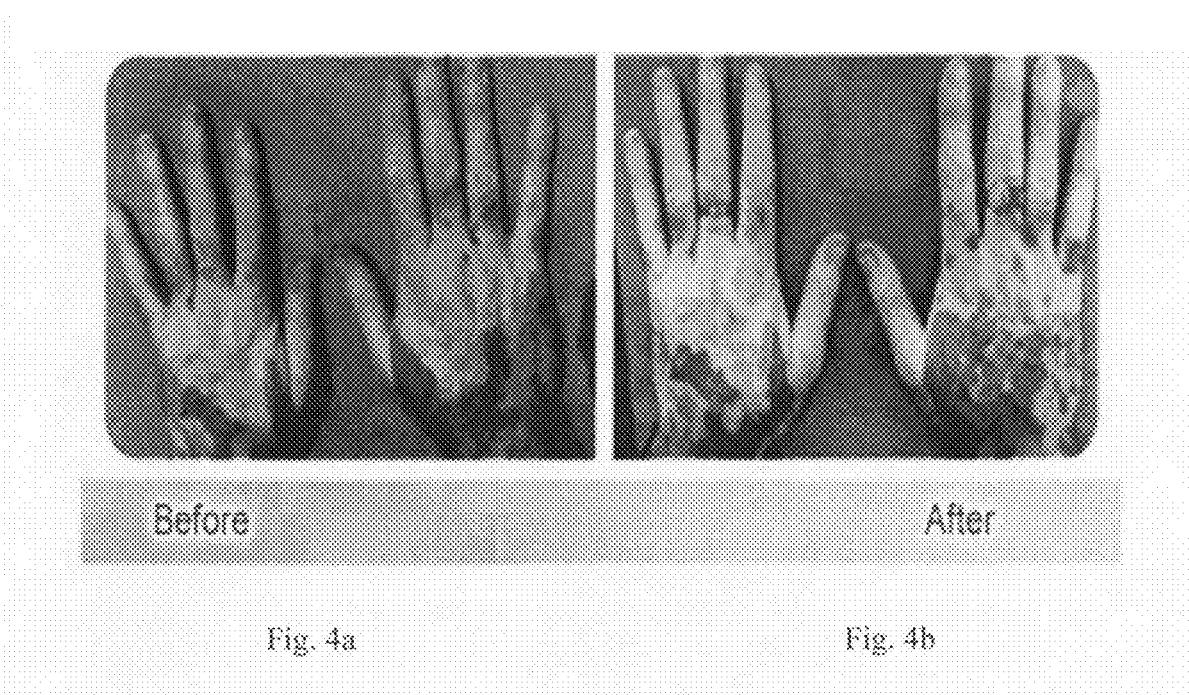
FIG. 4 (*a*) is the representation of vitilligo before the treatment with topical bFGF peptide lotion and PUVASOL.
Figures 5A, 5B:
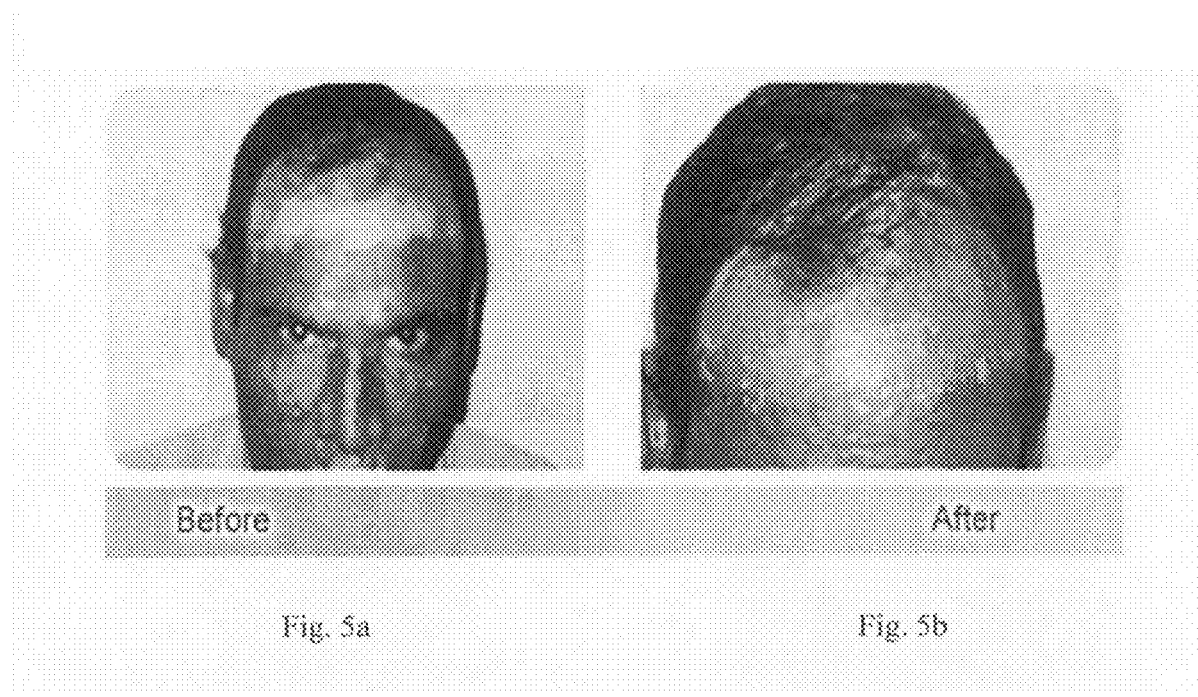
FIG. 5 (*a*) is the representation of vitilligo resistant for more than a year for PUV-A before treatment with topical peptide bFGF lotion and PUV-A.
Figures 6A, 6B:
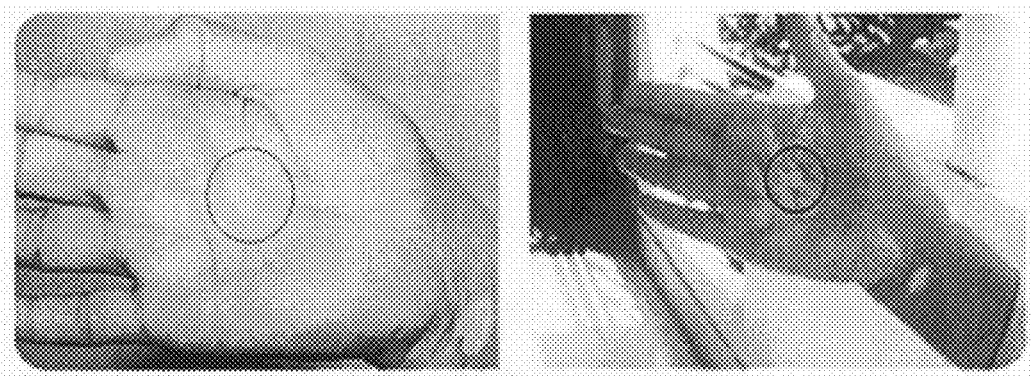
FIG. 6 (*a*) is the representation of vitilligo resistant for more than a year for PUV-A before the treatment with topical peptide bFGF lotion and PUV-A FIG. 6 (*b*) is the representation of vitilligo resistant for more than a year for PUV-A after the treatment with topical peptide bFGF lotion and PUV-A.
Figures 7A, 7B:
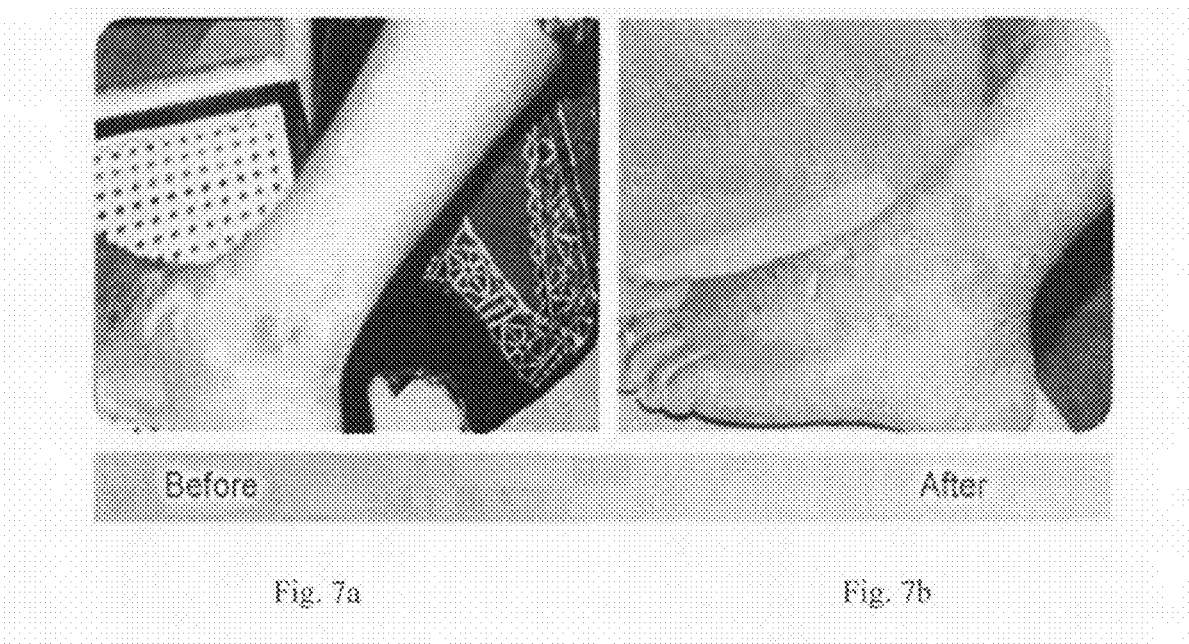
FIG. 7 (*a*) is the representation of vitilligo resistant for more than a year for PUV-A before treatment with topical peptide bFGF lotion and PUV-A FIG. 7 (*b*) is the representation of vitilligo resistant for more than a year for PUVA after the treatment with topical peptide bFGF lotion and PUVA.
Figures 8A, 8B:
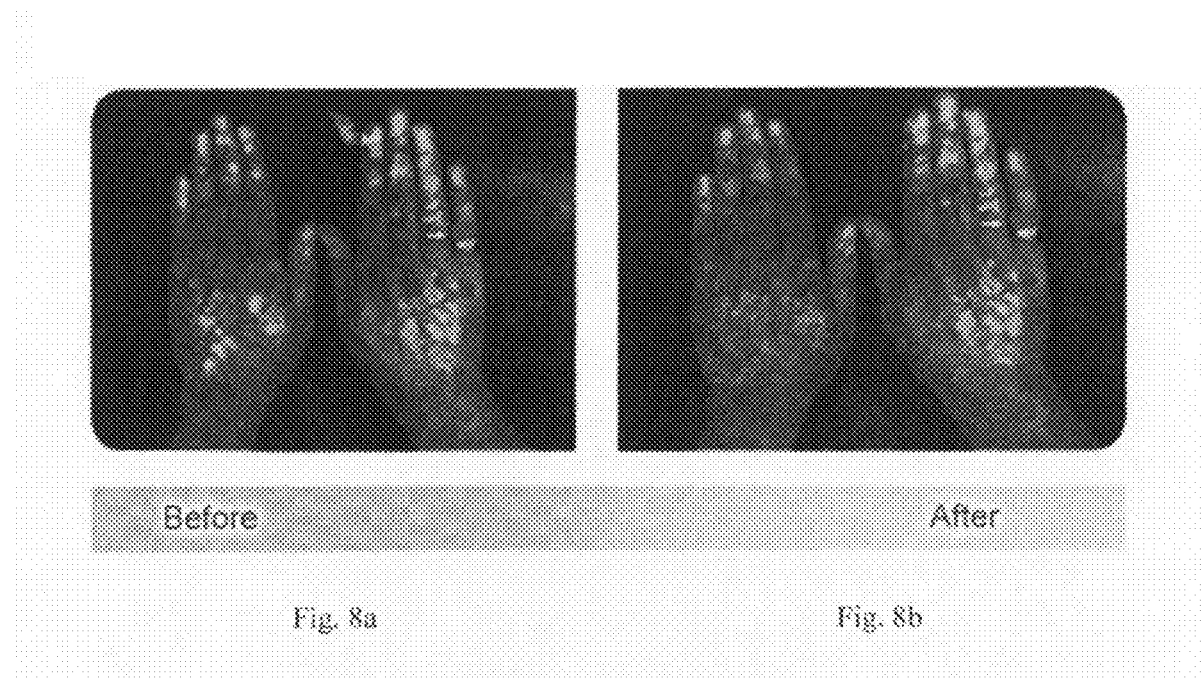
FIG. 8 (*a*) L is the representation of vitiligo after punch grafting but before start of the treatment with bFGF peptide lotion. R is the control.

That this happens was shown in a clinical trial on human volunteers. The above twin objectives were accomplished. A typical case of such treatment was shown in FIG. 2*a*, 2*b*. FIG. 2*a* describes two vitiligo patches at the start of treatment of oral steroids, while 2*b* describes the same patches at the end of 3 months of treatment with oral steroids while at the same time bFGF peptide(s) lotion was applied locally once a day on the lower vitiligo patch for the duration of intake of oral steroids. It can be clearly seen that there was faster repigmentation where bFGF peptide(s) lotion was applied as compared to the upper vitiligo patch where there was no application of bFGF peptide(s) lotion. The arrest of the fast spread of the disease was accomplished to the same extent of 88% at the end of 6 months of treatment with oral steroids and the result was not altered by the local application of bFGF peptide(s) lotion (See table 3 for more details)

At the end of 3 months of combinatorial treatment with steroids and local application of bFGF peptide(s) lotion more than 3 fold more patients got pigmented to a marked extent than with steroid alone (See Table 4 for more details). The percentage of volunteers who had moderate and marked rate of repigmentation with combinatorial therapy at the end of three months of treatment is twice than with the steroid therapy alone.

Synergistic Combinatorial Therapy for Treatment of Stable Vitiligo Comprising Local Application of the Peptide(s) in the Formulation Described in the U.S. Pat. No. 6,143,723 and Oral Psoralens Plus Application of UV-A.

The major or main stay of treatment of stable vitiligo all over the world is at present psoralens and UV-A therapy (Mofty E L, A preliminary clinical report on the treatment of leucoderma with ami Majus Linn. Jroy. Egypt. Med. Assoc, 1948, 651-660, Mofty E L, In Vitilligo, and psoralens 1968, Pregman Press Oxford, Ortonne J P, Bose Sk, Vitilligo, Wheree do we stand, Pig. Cell. Res 1993, 6, 61-72). However it is only partially effective (Westerhof Wiete, Ludmila Nieuwebor-krobotova, Treatment of vitilligo with UV-B radiation VS topical psoralen Plus UV-A. arch. Dermatol 1997, 1525-1528) and requires long duration of treatment. In addition it has many side effects particularly on liver and the risk of cancer in the Caucasian skin type 11 and 111 population (Henseleer T, Cristopher E, Honingsmann H, Wolff K, Skin tumors in European PUV-A study, 8 year follow up of 1643 patients treated with PUV-A for psoriasis J. Am. Acad. Dermatol 1997, 16, 108-116, Stern R S, Lard M, The carcinogenic risk of treatment for severe psoriasis photochemotherapy follow up study. 1994, 73, 2759-2764). Therefore there is indeed a need to reduce the a) Duration of the treatment
b) To increase success rate
c) To treat cases non responsive to PUV-A therapy.

The mechanism of action of psoralens and UV-A in repigmentation of vitiligo patches is still an enigma. Psoralens by themselves are ineffective in treating vitiligo unless followed by exposure of skin to UV-A (Gupta A K, Anderson T F, Psoralen photochemotherapy. J. Amer. Acad. Dermatol 1987, 17, 703-34). The absorption maxima of psoralens lie in the 210-330 nm range (Harbar L C, Bickeers. D R, "Photosensitivity Diseases" 1$^{st}$ edition Philadelphia: W.B. Saundeers 1981, PP 45-55) and the action spectrum of ingested psoralens is probably in the range of 320-335 nm (Flemming M G, Brody N, Biological effectiveness of black light fluorescent lamps for PUV-A. J. Amer. Acad. Dermatol, 1985, 12, 894). The psoralens induce skin photosensitization and involves inter-chelation of psoralens with the DNA of the cell, which leads eventually to the death of that cell. That this is true in the case of melanocytes also was shown by exposure of melanocytes in culture to PUV-A (KaoC, Yu H, Comparison of the effect 8-methoxy psoralen plus UV-A on human melonocytes in vitilligo vulgaris in-vitro. J. Invest. Dermatol. 1992, 98, 734-40). How to explain then the beneficial effects of PUV-A in increasing the proliferation of melanocytes, their migration to vitiligo patches and thus repigment vitiligo macules? The main target of PUV-A is the epidermis, which receives UV-A radiation. This could kill keratinocytes of the epidermis. The cellular contents of keratinocytes can then leak and stimulate the proliferation of the adjacent melanocytes. The cellular contents of keratinocytes include many mitogens to melanocytes in addition to bFGF (Halban R, Tyrrell L, Longely J, Yanden Y, Rubin J, Ann. NY. Acad. sci 1993, 680, 290-300). That the serum from successfully treated vitiligo patients with PUV-A stimulates the proliferation of melonacytes from normal untreated vitiligo patients was shown in 1989 (Ramaiah. A, Puri. N, Mojamdar M, A new hypothesis for the etiology of vitiligo, Acta Derm, Venerol (Stockholm), 1989, 69, 323-327).

In addition it was shown that the melonacytes from successfully treated vitiligo patients grow with less generation time than the melanocytes from the untreated normal individuals ((Ramaiah. A, Puri. N, Mojamdar M, A new hypothesis for the etiology of vitiligo, Acta Derm, Venerol (Stockholm), 1989, 69, 323-327).

These results indicated that the combinatorial treatment of vitiligo comprising local application of bFGF peptide(s) lotion with oral psoralens plus UV-A might act synergistically and produce faster repigmentation than with either of them alone.

Example: 3

That indeed the combinatorial therapy for treatment of vitiligo comprising local application of bFGF peptide(s) lotion and PUV-A works synergistically could be seen in the typical pictures shown in FIGS. 3a, 3b and 4a, 4b. The 3a and 4a are the pictures of two volunteers before the combinatorial treatment, while 3b and 4b are the pictures of the same volunteers respectively at the end of 3 months of combinatorial treatment where the right hand of each volunteer was in addition treated with the local application of bFGF peptide(s) lotion. As can be seen from the pictures, the right hands of both the volunteers treated in addition with the local application of bFGF peptide(s) lotion repigmented many times more than that of the left hands of both the volunteers, which were treated with the PUV-A therapy only. The data presented in Table 4 clearly indicate that 7 volunteers treated with combinatorial treatment with bFGF peptide(s) lotion and PUV-A had marked repigmentation in 3 months compared to only one with PUV-A. The percentage of volunteers who had moderate to marked rate of repigmentation with the combinatorial therapy at the end of three months is about twice than the number with PUV-A therapy alone (See Table 5 for details).

Synergistic Combinatorial Therapy for Treatment of Vitiligo not Responding to PUV-A Comprising Local Application of bFGF Peptide(s) and PUV-A Therapy.

In response to PUV-A therapy, less than 20% of vitiligo patches repigment fully, 30-40% of vitiligo patches repigment partially (Westerhof Wiete, Ludmila Nieuwebor-krobotova, Treatment of vitiligo with UV-B radiation VS topical psoralen Plus UV-A. arch. Dermatol 1997, 1525-1528). The vitiligo patches of volunteers, who did not respond PUV-A therapy even after prolonged treatment for a year or more were selected for the combinatorial therapy of local application of the bFGF agonist peptide(s) lotion with the continued PUV-A therapy.

Example: 4

The combinatorial therapy was very successful in repigmenting vitiligo patches with in 3 months which were unresponsive for more than year to PUV-A therapy. The typical results were shown in FIGS. 5a, 5b and 6a, 6b and 7a, 7b. The rate of repigmentation is indeed remarkable in 5a, 5b and 6a, 6b. It is also remarkable that the vitiligo patch in the palm which normally never responds to PUV-A therapy even after prolonged duration responded well to combinatorial therapy of bFGF peptide(s) lotion and PUV- A. The response to combinatorial therapy was shown in more than 90% of cases (See Table 6 for details).

The results presented here were not exhaustive. The combinatorial therapy with local application of bFGF peptide(s) in the formulation described in the U.S. Pat. No. 6,143,723 can be applied to almost any other therapy that are now in the market for the treatment of various types of vitiligo with synergistic effects similar to what was observed in the cases described above. The bFGF peptide(s) in the formulation may be applied locally not only in the form of a lotion but also in any other form like gel/ointment/cream with similar results.

Synergistic Combinatorial Therapy for the Treatment of Vitiligo Comprising Punch Graft Surgical Procedure/or Other Surgical Procedures Followed by the Local Application of bFGF Peptide(s).

Surgical procedures as mentioned earlier are resorted to as the last chance for the treatment of vitiligo patches. They include thrish grafting, expansion of autologus melanocytes in culture and their application on to derm-abraded vitiligo patch, autologus expansion of keratinocytes and melaonocytes in culture in the form of a multi cell layered sheets and their application on the derm-abraded vitiligo patches, or punch grafting of pigmented autologus skin on to the derm-abraded vitiligo patches. In all these cases, after the surgical procedures, the vitiligo patches were surgical bandaged with appropriate antibiotic regimen for the healing of the wounds. The wounds heal with in week or so. Then the local application of the bFGF peptide(s) in the formulation described in the U.S. Pat. No. 6,143,723 was done for 3 months. This results in faster repigmentation uniformly.

Example: 5

The photographs 8a and 8b describe the synergistic effect on increasing the rate of repigmentation in 8b where the local application of the bFGF peptide(s) in the formulation was done following the punch graft surgical procedure.

TABLE 1

Effect of Local Application of the Peptide on Repigmentation of all types of Vitiligo Patches of Volunteers

| Quality of Improvement | At 12 weeks | % of total | End of treatment | % of total | % significant repigmentation at end of treatment |
|---|---|---|---|---|---|
| Marked | 15 | 15.3 | 49 | 50 | 80 |
| Moderate | 31 | 31.6 | 29 | 30 | |
| Minimal | 52 | 53 | 20 | 20 | |
| Nil | 0 | | 0 | | |

TABLE 2

Effect of Local Application of the Peptide on Repigmentation of patches of Segmental Vitiligo of Volunteers

| Quality of Improvement | At 12 weeks | % of total | End of treatment | % of total | % significant repigmentation at end of treatment |
|---|---|---|---|---|---|
| Marked | 1 | 4.3 | 16 | 70 | 83 |
| Moderate | 8 | 34.7 | 3 | 13 | |
| Minimal | 14 | 60.8 | 4 | 17.4 | |

TABLE 3

Disease Activity of Vitiligo in Patients treat with either OMP of beta methasone or together with local application of the peptide

| | No. of patients where the disease was arrested with time | | | |
|---|---|---|---|---|
| Treatment Regimen | At 3 months | | At 6 months | |
| Active Peptide + OMP | 12 | 75% | 14 | 87.50% |
| OMP Alone | 12 | 75% | 14 | 87.50% |

TABLE 4

Effect of OMP of beta methasone and local application of the peptide on repigmentation of vitiligo patches of volunteers with time

| Treatment Regimen | At 3 months | | | At 6 months | | |
|---|---|---|---|---|---|---|
| | Minimal | Moderate | Marked | Minimal | Moderate | Marked |
| Active Peptide + OMP | 5 (31.25%) | 5 (31.25%) | 6 (37.5%) | 4 (25%) | 4 (25%) | 8 (50%) |
| OMP Alone | 11 (68.75%) | 3 (18.75%) | 2 (12.5%) | 8 (50%) | 4 (25%) | 4 (25%) |

TABLE 5

Effect of PUV-A Sol and local application of the peptide on repigmentation of vitiligo patches of volunteers with time

| Treatment Regimen | At 3 months | | | At 6 months | | |
|---|---|---|---|---|---|---|
| | Minimal | Moderate | Marked | Minimal | Moderate | Marked |
| Active Peptide + PUA-A Sol | 6 (33.3%) | 5 (27.7%) | 7 (38.8%) | 2 (11.1%) | 4 (22.2%) | 12 (66.6%) |
| PUV-A Sol Alone | 11 (61.1%) | 6 (33.3%) | 1 (5.5%) | 7 (38.8%) | 5 (27.7%) | 6 (33.3%) |

TABLE 6

Clinical Trial: Treatment of PUVA resistant Vitiligo by combination with the peptide(s)

| Name | Age/Sex/Start | Skin type | Location | Type | DOD/FH | pastRx/dur |
|---|---|---|---|---|---|---|
| Patient 1 | 35/F/3/8/99 | IV | Wrst, L.leg | V.Vulgaris | 10 yrs | PUVA/1.25 yrs |
| Patient 2 | 20/F/3/8/99 | III | lips, nostril | V.V/mucosl | 2 yrs | PUVA/1.25 yrs |
| Patient 3 | 30/F/3/8/99 | IV | lips, | V.V/Mucosl | 13 months | PUVA/1 yr |
| Patient 4 | 35/M/5/8/99 | IV | forehd/lips | V.V/mucosl | 4 yrs | PUVA/1.25 yrs |
| Patient 5 | 34/M/5/8/99 | | | | | |
| Patient 6 | 29/F/14/8/99 | IV | lips | V.V/Mucosl | 15 yrs | PUVA/1 yr |
| Patient 7 | /F/7/8/99 | IV | Lips | V.V/mucosl | 6 yrs | PUVA/.1/2 yr |
| Patient 8 | 20/F/3/8/99 | IV | lips/cheek | V.V/mucosl | 12 yrs | PUVA/grft |
| Patient 9 | 24/F/7/8/99 | IV | lips/cheek | V.V/mucosl | 18 yrs | PUVA/1.75 yrs |
| Patient 10 | 52/M/4/8/99 | IV | Wrist | V.V/wrist | >10 yrs | PUVA/1.5 yrs |
| Patient 11 | 22/M/24/8/99 | IV | L.Cheek | V.V/seg | 15 yrs | PUVA/1.25 yrs |
| Patient 12 | 35/M/30/8/99 | IV | chin/ebrow | V.V | 30 yrs/+ | PUVA/>1 yr |
| Patient 13 | 22/M/28/8/99 | IV | leg | V.V | 2 yrs | PUVA/0.5 yr |
| Patient 14 | 36/M/27/7/99 | 1V | Rwrist/lip | V.V/mucosal | 15 yrs | PUVA/1.25 yrs |
| Patient 15 | /F/27/7/99 | | | | | |
| Patient 16 | 30/F/27/7/99 | IV | F.tips/lips | V.V/mucosl | 10 yrs | PUVA/1 yr |
| Patient 17 | 30/F/21/9/99 | 1V | lips/filcrum | V.V/mucosl | 10 yrs/+ | PUVA/0.6 yr |
| Patient 18 | 45/F/21/9/99 | IV | lips/wrist | V.V/mucosl | 2 yrs | PUVA/0.5 yr |
| Patient 19 | 48/M/21/9/99 | IV | lips/palm | V.V/mucosl | 10 yrs | PUVA |

| Name | Response | Present Res | durRx | UVA Dose 2/week | |
|---|---|---|---|---|---|
| Patient 1 | 70% | 4+ | 3 months | 4.5 J/cm2 | |
| Patient 2 | 50% | 3+ | 3 months | 5 J/cm2 | |
| Patient 3 | 50% | 2+ | 3 months | 3 J/cm2 | |
| Patient 4 | 50% | 4+/3+ | 3 months | 8 J/cm2 | |
| Patient 5 | | Irglr/dropped. | | | |
| Patient 6 | 80% | 2+ | 3 months | 8 J/cm2 | |
| Patient 7 | 80% | Irglr/dropped. | | | |
| Patient 8 | 80% | Irglr/dropped. | | | |
| Patient 9 | 80% | 2+ | 3 months | 7.5 J/Cm2 | |
| Patient 10 | dropped | | | 7.5 J/cm2 | |
| Patient 11 | 80% | 1+ | 2 months | 8.5 J/cm2 | incmplt appl |
| Patient 12 | <50% | 2+ | 2.5 months | 9 J/cm2 | |
| Patient 13 | | 2+ | 2.5 months | 9.5 J/cm2 | |
| Patient 14 | 80% | 2+ | 3 months | 8.5 J/cm2 | |
| Patient 15 | | Irglr/dropped. | | | |
| Patient 16 | 80% | 2+ | 3 months | 8 J/cm2 | Tips imprvd |
| Patient 17 | 50% | 1+ | 2 months | 8.5 J/cm2 | |
| Patient 18 | 70% | 2+ | 2 months | 6.5 J/cm2 | |
| Patient 19 | 70% | 2+ | 2 months | 9.5 J/cm2 | |

Grade, 0.0 = no pigmentation, 1 = minimal pigmentation, 2+ = moderate rate of pigmentation, 3 = rapid rate of pigmentation, 4+ = very rapid rate of pigmentation
DOD = Duration of the disease,
F.H = Family history is positive when + is given.
All the cases dropped from the trial has no relation to the response of treatment.

The invention claimed is:

1. A method for combinatorial synergistic therapy for treatment of generalized stable vitiligo and segmental vitiligo, comprising applying an effective amount of a composition comprising 0.02 to 5% w/w of at least one peptide selected from the group consisting of bFGF amino acids 106-115 (SEQ ID NO: 1), bFGF amino acids 106-120 (SEQ ID NO: 5), bFGF amino acids 1-24 (SEQ ID NO: 6) and SEQ ID NOS: 2, 3, 4, 7, and 8, along with psoralens and UV-A of sun light (PUVASOL), wherein said applying step is done for three months.

2. A method for combinatorial synergistic therapy for treating a subject with vitiligo patches not responding to PUV-A therapy, comprising applying an effective amount of a composition comprising 0.02-5% w/w of at least one peptide selected from the group consisting of bFGF amino acids 106-115 (SEQ ID NO: 1), bFGF amino acids 106-120 (SEQ ID NO: 5), bFGF amino acids 1-24 (SEQ ID NO: 6) and SEQ ID NOS: 2, 3, 4, 7, and 8, along with psoralens and UV-A (PUV-A) to a subject having vitiligo patches who was not responding to PUV-A therapy, wherein said applying step is done for three months.

3. A method for combinatorial synergistic therapy for treatment of fast spreading vitiligo comprising local application of an effective amount of a composition comprising 0.02-5% w/w of at least one peptide selected from the group consisting of bFGF amino acids 106-115 (Seq ID NO 1), bFGF amino acids 106-120 (Seq ID NO 5), bFGF amino acids 1-24 (Seq ID NO 6) and Seq IDS NOS: 2, 3, 4, 7, and 8, along with oral steroid therapy.

4. A method for combinatorial synergistic therapy for treatment of generalized stable vitiligo, fast-spreading vitiligo or segmental vitiligo, comprising topically applying an effective amount of a composition comprising 0.02 to 5% w/w of at least one peptide selected from the group consisting of bFGF amino acids 106-115 (SEQ ID NO: 1), bFGF amino acids 106-120 (SEQ ID NO: 5), bFGF amino acids 1-24 (SEQ ID NO: 6) and SEQ ID NOS: 2, 3, 4, 7 and 8, and further comprising administering an effective amount of a psoralen, a steroid, or a surgical therapy, wherein said topically applying step and said administering step are done for three months.

5. The method according to claim 4, wherein said psoralen comprises a topical psoralen and UV-A/UV-B, wherein said steroid comprises a local steroid therapy, and wherein said surgical therapy comprises a surgical punch graft procedure.

* * * * *